(12) United States Patent
Wilhelm et al.

(10) Patent No.: US 6,624,169 B1
(45) Date of Patent: Sep. 23, 2003

(54) UROKINASE INHIBITORS (75) Inventors: Olaf Wilhelm, München (DE); Viktor Magdolen, Kirchheim (DE); Jörg Stürzebecher, Erfurt (DE); John Foekens, Capelle a/d Ijssel (NL); Verena Lutz, München (DE)

(73) Assignee: Wilex Biotechnology GmbH, München (DE)

( * ) Notice: Subject to any disclaimer, the term of this patent is extended or adjusted under 35 U.S.C. 154(b) by 0 days.

(21) Appl. No.: 09/743,800

(22) PCT Filed: Jul. 20, 1999

(86) PCT No.: PCT/EP99/05145

§ 371 (c)(1),
(2), (4) Date: Apr. 3, 2001

(87) PCT Pub. No.: WO00/04954

PCT Pub. Date: Feb. 3, 2000

(30) Foreign Application Priority Data

Jul. 20, 1998 (EP) ............................. 98113519

(51) Int. Cl.$^7$ ................ A61K 31/495; A61K 31/445; A61K 31/195; A61K 47/48

(52) U.S. Cl. ............. 514/255.01; 544/388; 546/226; 514/330

(58) Field of Search ............ 544/388; 514/255.01, 514/330; 546/226

(56) References Cited

FOREIGN PATENT DOCUMENTS

| | | | |
|---|---|---|---|
| DE | 30 35 086 | | 4/1981 |
| DE | WO 94/18185 | * | 8/1994 |
| EP | 0 183 271 | | 6/1986 |
| WO | 92/08709 | | 3/1992 |
| WO | 95/17885 | | 7/1994 |
| WO | 94/18185 | | 8/1994 |
| WO | 96/05189 | | 2/1996 |
| WO | WO 00/17158 | | 3/2000 |

OTHER PUBLICATIONS

Sturzebecher et al. Synthesis and structure–activity relations of potent thrombin inhibitors:pioerazides of 3–amidinophenylalanine. J. Med. Chem. 40: 3091–3099, 1997.*

CAS pintout for CH 689611, 1999.*

Pentapharm Product Catalog 1998.

* cited by examiner

*Primary Examiner*—Mukund J. Shah
*Assistant Examiner*—Hong Liu
(74) *Attorney, Agent, or Firm*—Rothwell, Figg, Ernst & Manbeck, PC (57) ABSTRACT

The invention relates to the use of derivatives of 3-amidinophenylalanine as urokinase inhibitors for treating malignant tumors and the formation of metastases.

14 Claims, 6 Drawing Sheets

UROKINASE INHIBITORS

The invention relates to the use of derivatives of 3-amidinophenylalanine as urokinase inhibitors in particular for treating malignant tumors and the formation of metastases or as agents for targeting lymphocytes and for treating disorders of the lymphatic tissue, in particular lymphomas.

The ability of solid tumors to spread and metastasize in surrounding tissue correlates with the degradation or transformation of the extracellular matrix (tumor stroma) in the vicinity of the tumor cell and/or with the ability of said tumors to penetrate the basement membrane. Although the (patho)biochemical connections have not been completely elucidated yet, the plasminogen activator urokinase (uPA) and the urokinase receptor (uPAR) play a central role. uPA mediates the proteolytic cleavage of plasminogen to give plasmin. Plasmin in turn is a protease which has a wide range of actions and is capable of directly breaking down components of the extracellular matrix such as fibrin, fibronectin, laminin and the protein skeleton of proteoglycans. In addition, plasmin can activate "latent" metalloproteases and the inactive proenzyme of uPA, pro-uPA.

Tumor cells and non-malignant cells of the tumor stroma synthesize and secrete the enzymatically inactive proenzyme pro-uPA. Proteases such as, for example, plasmin or the cathepsins B and L cleave pro-uPA by limited proteolysis to give the active serine protease HMW-uPA (HMW=high molecular weight). Pro-uPA and the active protease HMW-uPA bind to the cell surface receptor uPAR (CD87). Plasmin(ogen) likewise binds to specific receptors on the plasma membranes of tumor cells which leads to focused and amplified plasminogen activation in the immediate vicinity of the tumor cells. Invasive cells thus are able to break down the extracellular matrix without finding themselves deprived of the support necessary for directed movement because of proteolysis.

Various cytobiological studies have shown that the cell-associated plasminogen activator system is of particular importance within the cascade-like reaction pathways of tumor-associated proteolytic systems (Wilhelm et al. (1994 The Urokinase/Urokinase receptor system: A new target for cancer therapy? In: Schmitt M., Graeff H., Kindermann G. (eds.): Prospects in Diagnosis and Treatment of Cancer. International Congress Series, Excerpta Medica 1050, Amsterdam, Elsevier 1994, pp 145–156). Cultures of human colon carcinoma cells showed that their ability to migrate through an extracellular matrix depended on the degree of uPA receptor saturation with active uPA. (Hollas et al., Cancer Res. 51 (1991), 3690–3695). The cell culture model likewise showed a reduction in the invasive potential of cells when PAI-1 (Cajot et al., Proc. Natl. Acad. Sci. USA 87 (1990), 6939–6943) or PAI-2 (Baker et al., Cancer Res. 50 (1990), 4676–4684) inhibited the proteolytic activity of uPA. A similar effect was achieved on inhibition of uPA binding to the cell surface by blocking the receptor by means of proteolytically inactive uPA variants (Cohen et al., Blood 78 (1991), 479–487; Kobayashi et al., Br. J. Cancer 67 (1993), 537–544). Transfection of epidermoid carcinoma cells using a plasmid expressing an antisense transcript of a part of uPAR also reduced the invasivity of said cells by suppressing uPAR synthesis (Kook, EMBO J. 13 (1994), 3983–3991). Antibodies directed against uPA and PAI-1 reduced the invasive potential of lung cancer cells in vitro (Liu et al., Int. J. Cancer 60 (1995), 501–506).

Animal models of tumors were also able to show the influence of the plasminogen activator system on the metastasizing process. Thus, addition of anti-uPA antibodies almost completely prevented the formation of lung metastases caused by human carcinoma cells in chicken embryos (Ossowski and Reich, Cell 35 (1983), 611–619). Metastasizing human carcinoma cells were transfected using an expression plasmid which encoded a proteolytically inactive, but uPAR-binding uPA mutant. The mouse model showed that carcinoma cells synthesizing inactive uPA produced a significantly smaller number of metastases after injection than nontransfected cells (Crowley et al., Proc. Natl. Acad. Sci. USA 90 (1993), 5021–5025). Moreover, after administration of uPA antisense oligonucleotides, nude mice showed inhibition of intraperitoneal spreading of human ovarian carcinoma cells (Wilhelm et al., Clin. Exp. Metast. 13 (1995), 296–302).

In recent years, the clinical relevance of factors of the plasminogen activator system (uPA, uPAR, PAI-1 and PAI–2) for the prognosis of patients having solid malignant tumors has been intensively studied. In these studies, the uPA antigen content in various tumors (e.g. breast, ovaries, stomach, lung, kidney) proved to be a strong prognostic factor both for the recurrence-free survival and for the mortality (see for example, Schmitt et al., J. Obstet. Gynaecol. 21 (1995), 151–165; Jaenicke et al., Breast Cancer Res. Treat. 24 (1993), 195–208; Kuhn et al., Gynecol. Oncol. 55 (1994), 401–409; Nekarda et al., Lancet 343 (1994), 117; Pedersen et al., Cancer Res. 54 (1994), 4671–4675). Likewise, increased concentrations of uPAR in lung cancer tissue (Pedersen et al., supra) and breast cancer tissue (Duggan et al., Int. J. Cancer 61 (1995), 597–600; Ronne et al., Breast Cancer Res. Treat. 33 (1995), 199–207) and also in the case of stomach cancer both in the tumor tissue itself (Heiss et al., J. Clin. Oncol. 13 (1995), 2084–2093) and in tumor cells disseminated into bone marrow (Heiss et al., Nature Medicine 1 (1995), 1035–1039) correlate with a poor prognosis.

The use of synthetic uPA inhibitors makes it possible to suppress invasion and spreading of tumor cells. However, developing specific uPA inhibitors is difficult, since tissue plasminogen activator (tPA) has an identical specificity for cleaving the peptide bond Arg560/Val561 of plasminogen. In most cases therefore, low molecular weight uPA inhibitors also inhibit tPA and thus also tPA-mediated fibrinolysis. In addition, it must be guaranteed that synthetic uPA inhibitors show no strong plasmin inhibition.

Despite these restrictions, some inhibitors are known which have a certain specificity for uPA, but a low inhibition capacity, such as benzamidine derivatives and β-naphthamidine derivatives, the most effective compound inhibiting uPA with $K_i$=2.2 μmol/l (Stürzebecher and Markwardt, Pharmazie 33 (1978), 599), or amiloride with $K_i$=7 μmol/l (Vassalli and Belin, FEBS. Lett. 214 (1987), 187–191).

DE-A-30 35 086 discloses cyclohexanecarboxylic acid derivatives which have inhibitory effects on proteases such as trypsin, chymotrypsin, thrombin or uPA. However, the compounds studied only show quite weak and, moreover, unspecific uPA inhibition. EP-A-0 183 271 discloses lysine derivatives and the use thereof as protease inhibitors. A benzamidinolysine derivative (compound 108) is also described which inhibits uPA in vitro, but acts comparably on other proteases such as trypsin or plasma kallikrein. WO 95/17885 discloses low molecular weight polypeptides as uPA inhibitors.

Another class of known uPA inhibitors is represented by 4-substituted benzothiophene-2-carboxamidines with $K_i=0.16$ mmol/l in the case of benzothiophene 623 (Towle et al., Cancer Res. 53 (1993), 2553–2559). These inhibitors have a significantly higher affinity for uPA than for tPA and plasmin. uPAR-bound uPA, too, is inhibited very effectively. Disadvantageously however, the chemical synthesis of these substances is complicated and few possibilities for structural modifications are present or have been demonstrated until now.

Therefore, the development of further uPA inhibitors is very beneficial for further elucidating the role of uPA and uPAR in various diseases, especially in tumor spreading and metastasizing.

Nα-Arylsulfonyl and Nα-arylsulfonylaminoacyl derivatives of 3-amidinophenylalanine are known as selective inhibitors of thrombin (Markwardt et al., Thromb. Res. 17 (1980), 425–431) or of coagulation factor Xa (Stürzebecher et al., Thromb. Res. 54 (1989), 245–252). WO 92/08709, WO 94/18185 and WO 96/05189 also disclose the use of amidinophenylalanine derivatives as inhibitors of blood clotting, in particular as inhibitors of thrombin.

Piperidides and piperazides of 3-amidinophenylalanine have been intensively studied, among which lead structures for inhibiting fibrinolytic enzymes have been found (Stürzebecher et al., J. Enzyme Inhibition 9, 87–99, 1995; Stürzebecher et al., J. Med. Chem. 40, 3091–3099, 1997). While Stürzebecher et al. (1995) merely describe inhibition of thrombin, factor Xa, plasmin and trypsin, Stürzebecher et al. (1997) also provide information about inhibiting uPA. Nα-2-Naphthylsulfonyl-, Nα-2-(2,2,5,7,8-pentamethylchroman-6-yl)sulfonyl-and Nα-2-camphor-10-yl-sulfonyl-substituted 3-amidinophenylalaninepiperazides have a $K_i$ for uPA of from 28 to 140 μmol/l, which is about three orders of magnitude higher than the inhibition constant for thrombin. Thus it was impossible to assume that 3-amidinophenylalanine derivatives are suitable as urokinase inhibitors.

Surprisingly we have found, however, that 3-amidinophenylalanine derivatives substituted in the 2 position by a phenyl radical represent selective uPA inhibitors which are active in vivo. Furthermore, we have found that these substances have high selectivity for lymphatic tissue and thus are suitable as agents for targeting lymphocytes, for example for treating malignant disorders of the lymphatic tissue such as lymphomas.

The present invention relates to novel urokinase inhibitors of the general formula I, which are derived from 3-amidinophenylalanine and are present as racemates and also as L- or D-configured compounds and in which

$R^1$ (a) is OH or $OR^4$, where $R^4$ is unsubstituted or substituted, for example by hydroxyl, carboxyl, sulfonyl, nitro, cyano, oxo and/or halogen, branched or unbranched $C_1$–$C_8$-alkyl, $C_3$–$C_8$-cycloalkyl or aralkyl, e.g. benzyl or phenylethyl, (b) represents a group of the formula in which $R^5$ and $R^6$ are any radicals compatible with the overall structure, where in particular
(i) $R^5$ and $R^6$ are H,
(ii) $R^5$ is H and $R^6$ is unsubstituted or substituted, for example by hydroxyl, carboxyl, sulfonyl, nitro, cyano, oxo and/or halogen, branched or unbranched $C_1$–$C_8$-alkyl, aralkyl, e.g. benzyl or phenylethyl, or $C_5$–$C_8$-cycloalkyl,
(iii) $R^5$ and $R^6$ are in each case independently unsubstituted or substituted, for example by hydroxyl or/and halogen, unbranched or branched $C_1$–$C_4$-alkyl or
(iv) $R^5$ is H and $R^6$ is —$NH_2$ or is, in particular, an aryl-substituted or heteroaryl-substituted amino group,
(v) $R^5$ is H or unsubstituted or substituted, for example by hydroxyl or/and halogen, unbranched or branched $C_1$–$C_4$-alkyl, and $R^6$ is an amino acid residue, for example an α-, β- or ω-amino carboxylic acid or amino sulfonic acid residue, a peptide residue, for example of up to 50 amino acids in length, or a polypeptide residue, for example of from greater than 50 amino acids to 1000 amino acids in length, (c) represents a group of the formula in which m is the number 1 or 2 and in which one or more of the methylene groups are optionally substituted, for example by hydroxyl, carboxyl, $C_1$–$C_4$-alkyl or aralkyl, e.g. benzyl or phenylethyl, with the group (c) being racemic or in D or L configuration, and $R^7$ has the meaning of $R^1$ in subsections (a), (b) and (f),
(d) represents a group of the formula in which p=r=1, p=1 and r=2 or p=2 and r=1 and in which one or more of the methylene groups are optionally substituted, for example by hydroxyl, carboxyl, $C_1$–$C_4$-alkyl or aralkyl, e.g. benzyl or phenylethyl, and $R^7$ has the meaning of $R^1$ in subsections (a), (b) and (f),
(e) represents a piperidyl group which is unsubstituted or substituted in one of positions 2, 3 or 4, for example by $C_1$–$C_4$-alkyl, $C_1$–$C_3$-alkoxy or hydroxyl, where a further aromatic or cycloaliphatic ring, preferably phenyl or cyclohexyl, is optionally fused to the heterocycloaliphatic rings of the formulae (c), (d) and (e) in the 2,3 position or the 3,4 position relative to the heteroatom,
(f) represents a group of the formula in which $R^8$ is
  (i) unsubstituted or, for example, $C_1$–$C_6$-alkyl-, $C_1$–$C_3$-alkoxy-, hydroxyl-, carboxyl, sulfonyl-, nitro-, cyano-, oxo- or/and halogen-substituted $C_1$–$C_6$-alkyl or aryl, such as, for example, phenyl, p-halophenyl or naphthyl,
  (ii) saturated or unsaturated, branched or unbranched $C_1$–$C_6$-alkoxy or
  (iii) unsubstituted or, for example, $C_1$–$C_6$-alkyl-, $C_1$–$C_3$-alkoxy-, hydroxyl-, carboxyl-, sulfonyl-, nitro-, cyano-, oxo- or/and halogen-substituted phenoxy or benzyloxycarbonyl,
(g) represents an acyl radical of the formula —COX, where X is
  (i) H or unsubstituted, for example hydroxyl-, carboxyl-, sulfonyl-, nitro-, cyano-, oxo- or/and halogen-substituted, unbranched or branched alkyl, preferably $C_1$–$C_6$-alkyl, in particular methyl,
  (ii) unsubstituted or, for example, $C_1$–$C_6$-alkyl-, $C_1$–$C_3$-alkoxy-, hydroxyl-, carboxyl-, sulfonyl-, nitro-, cyano-, oxo- or/and halogen-substituted aryl or heteroaryl, such as, for example, phenyl, p-halophenyl or thienyl, or
  (iii) unsubstituted or, for example, hydroxyl-, carboxyl-, sulfonyl-, nitro-, cyano-, oxo- or/and halogen-substituted cycloalkyl, preferably $C_3$–$C_{10}$-cycloalkyl,
(h) represents aralkyl, e.g. benzyl or phenylethyl, in which the aromatic radical is unsubstituted or substituted, for example by halogen, $C_1$–$C_6$-alkyl, $C_1$–$C_3$-alkoxy, hydroxyl, cyano, carboxyl, sulfonyl or nitro,
(i) represents a carboxamide radical of the formula —CONR'R" a thiocarboxamide radical —CSNR'R", or an acetamide radical —$CH_2$—CONR'R" where
  (i) R' and R" are H,
  (ii) R' and R" are in each case independently $C_1$–$C_4$-alkyl,
  (iii) R' is H and R" is $C_1$–$C_4$-alkyl,
  (iv) R' is H and R" is aryl, e.g. phenyl, or
  (v) R' and R" constitute together with the nitrogen atom a heterocycloaliphatic ring having 5–7 ring members and possibly having a further heteroatom, e.g. N, O or/and S,
(j) represents $SO_2$—Y where Y is
  (i) unsubstituted or, for example, hydroxyl-, carboxyl-, sulfonyl-, nitro-, cyano-, oxo- or/and halogen-substituted $C_1$–$C_8$-alkyl, preferably methyl, trifluoromethyl, trichloromethyl,
  (ii) unsubstituted or, for example, $C_1$–$C_6$-alkyl-, $C_1$–$C_3$-alkoxy-, hydroxyl-, carboxyl-, sulfonyl-, nitro-, cyano-, oxo- or/and halogen-substituted aryl or heteroaryl, such as, for example, phenyl, 4-methylphenyl, 2,4,6-trimethylphenyl, 2,4,6-triisopropylphenyl, 4-methoxy-2,3,6-trimethylphenyl, 2,2-dimethyl-6-methoxychromanyl, 2,2,5,7,8-pentamethylchromanyl, anthraquinonyl, naphthyl or quinolyl, or O-aryl, preferably O-phenyl or O-heteroaryl or
  (iii) —NR'R", where R' and R" are in each case independently H or $C_1$–$C_3$-alkyl,
(k) represents a cycloaliphatic ring having from 5 to 8 carbon atoms, which is unsubstituted or substituted, for example by $C_1$–$C_6$-alkyl, $C_1$–$C_3$-alkoxy, halogen, hydroxyl or/and oxo,
(l) represents an unsubstituted or, for example, $C_1$–$C_6$-alkyl-, $C_1$–$C_3$-alkoxy-, hydroxyl-, carboxyl-, sulfonyl-, nitro-, cyano-, oxo- or/and halogen-substituted heteroaryl radical such as, for example, pyridyl or pyrimidyl, or heterocycloaliphatic radical, for example N-methylpiperidyl,
(m) represents a functionalized alkyl radical of the formula —$(CH_2)_n$—X, where the alkyl chain is unbranched or branched, n=1 to 8, and the functional radical X
  (i) represents a hydroxyl group whose hydrogen atom is unsubstituted or substituted by $C_1$–$C_4$-alkyl, aralkyl, e.g. benzyl or phenylethyl, aryl, e.g. phenyl, $C_1$–$C_4$-hydroxyalkyl or acyl group CO-alkyl, ($C_1$–$C_6$)
  (ii) is a halogen atom,
  (iii) represents a tertiary amino group of the formula —$N(alk)_2$, where the alkyl groups have 1 to 3 carbon atoms and are preferably the same, and the nitrogen atom may belong to a heterocycloaliphatic ring having 5–7 ring members and possibly having a further heteroatom, e.g. N, O or/and S,
$R^2$ represents unsubstituted or, for example, $C_1$–$C_6$-alkyl-, $C_1$–$C_3$-alkoxy-, hydroxyl-, carboxyl-, sulfonyl-, nitro-, cyano-, oxo- or/and halogen-substituted phenyl, such as, for example, phenyl, 4-methylphenyl, 2,4,6-trimethylphenyl, 2,4,6-tri-isopropylphenyl, 4-methoxy-2,3,6-trimethylphenyl,
$R^3$ is H or branched or unbranched $C_1$–$C_4$-alkyl, and n is 0 or 1.

The compounds may also be present as salts, preferably as physiologically acceptable acid salts, for example as salts of mineral acids, particularly preferably as hydrochlorides, or as salts of suitable organic acids.

Of the compounds defined in the general claims, those are of particular importance in which $R^1$ corresponds to a group of the formulae (b), (d) and (f), $R^2$ represents phenyl mono-, di- or trisubstituted by alkyl, in particular 2,4,6-substituted phenyl, e.g. 2,4,6-triisopropylphenyl, and n=0.

It is possible to prepare the compounds of the general formula I in a manner known in principle, for example as described in WO 92/08709 and WO 94/18185, and to assay their biological in vitro activity.

(L)-, (D) or (D,L)-3-cyanophenylalanine methyl ester hydrochloride is reacted with an appropriate sulfonyl chloride or a sulfonated amino acid or the halide thereof in the presence of a base to give a compound of the general formula I, which has a cyano function and in which $R^1=OCH_3$ and $R^2$ and also $R^3$ and n correspond to the meanings defined in the general claims. Mild acidic or alkaline hydrolysis produces therefrom the compounds of the general formula I, which have carboxylic acid structure ($R^1=$—OH) and whose acid-catalyzed esterification with an appropriate alcohol leads to compounds of the general formula I, where $R^1=$(a). Applying a method common in peptide chemistry, for example DCC in the presence of HOBt, reacting the carboxylic acids of the general formula I ($R^1=$OH) with a nucleophile of the structures (b), (e) and (f) may give compounds with the corresponding $R^1$ of the general formula I. To synthesize compounds with $R^1=$(c) and (d), carboxylic acids of the general formula I with $R^1=$OH are first reacted with cycloaliphatic amino acid esters of the structures (c) and (d), where $R^7$ is preferably —$OCH_3$ or $OC_2H_5$, the carboxylic esters obtained are hydrolyzed under mild acidic or alkaline conditions to give the corresponding carboxylic acids which may subsequently be esterified in a manner already described or be reacted with nucleophiles of the structures (b), (e) and (f), and compounds of the general formula I with $R^1=$(c) and also (d) and with $R^7=$(a), (b), (e) and (f) are obtained.

The target compounds of the general formula I, which have amidine structure, are obtainable from the cyano compounds in a known manner; normally, the thioamides are obtained first by addition of $H_2S$ to the cyano group, and are converted by S-methylation with methyl iodide into the thioimido esters and then into the amidino compounds by treatment with ammonium acetate in alcoholic solution. In addition and where appropriate, it is possible, using methanol or ethanol in the presence of HCl gas and, in particular cases, of an inert solvent, to prepare from the cyano compounds the corresponding imido ester hydrochlorides, which are reacted in alcoholic ammonia solution to give the amidino compounds.

The urokinase inhibitors according to the invention may be used, where appropriate, together with at least one suitable pharmaceutical excipient or carrier for producing orally, subcutaneously or intravenously administrable medicaments for controlling tumors or for diagnosis. Likewise possible is administration in combination with other active substances, for example other urokinase inhibitors such as antibodies or/and peptides.

The medicaments for controlling tumors in humans and animals may be administered topically, orally, rectally or parenterally, e.g. subcutaneously or intravenously, in the form of tablets, coated tablets, capsules, pellets, suppositories, solutions or transdermal systems such as plasters.

A particularly preferred compound of the formula (I) is Nα-(2,4,6-triisopropylphenylsulfonyl)-3-amidino-(D,L)-phenylalanine 4-ethoxycarbonylpiperazide hydrochloride or the L enantiomer thereof or a pharmaceutically suitable salt of these compounds. These substances have good solubility. They are soluble in Tris buffer (pH 7.3) up to a concentration of $5 \times 10^{-5}$ mol/l. Addition of 5% ethanol increases the solubility to $2 \times 10^{-4}$ mol/l and addition of 5% DMSO to $10^{-3}$ mol/l.

The compounds of the invention are capable of very effectively inhibiting the growth or/and spreading of malignant tumors, for example tumor spreading of pancreatic carcinoma, tumor growth of breast carcinoma and also metastasizing of tumors. It is possible to use the uPA inhibitors, where appropriate, together with other anti-tumor agents or with other types of treatment, e.g. radiation or surgery. Furthermore, the inhibitors according to the invention are also effective in other uPA-associated disorders (e.g. in preventing formation of blisters in the case of the skin disorder pemphigus vulgaris).

uPA inhibitors according to the invention are preferably characterized in that they have a $K_i$ which is at least twofold, preferably at least 5-fold and particularly preferably at least 10-fold lower for uPA than for tPA. It is furthermore remarkable that the compounds of the invention only marginally affect blood clotting, since their $K_i$ is too high for effective inhibition of thrombin and factor Xa.

The inventive substances of the formula I may be used in the form of conjugates with physiologically active substances, for example with radiolabels or cytotoxic agents, e.g. chemotherapeutics such as cisplatin or 5-fluorouracil, or with peptides. Furthermore it is possible to incorporate the substances into the membrane of carrier vesicles, e.g. liposomes, and thus to facilitate targeting of active substances enclosed in the carrier vesicles, for example cytotoxic agents such as doxorubicin.

Another indication for the substances of the general formula II:

$$X-R^2,$$

where X is any radical, in particular an organic radical, for example a radical as defined for compounds of the formula I, but also another radical, for example a physiologically active substance such as a cytotoxic agent, a peptide or a radiolabel, a lipid or a carbohydrate, and $R^2$ is a group as defined above, in particular 2,4,6-trisubstituted phenyl, e.g. 2,4,6-triisopropylphenyl, is the targeting of lymphocytes, which is possible owing to a 10- to 20-fold higher affinity of said substances for lymph node tissue than for other types of tissue. $R^2$ is preferably linked to the radical X via an —$SO_2$— sulfonyl group. Thus, these substances are excellently suited as diagnostic agents or as agents for treating diseases of the lymphatic tissue, in particular malignant diseases such as tumor metastases and lymphomas. Administering the substances may be carried out as already described above. Diseases of the lymphatic tissue are preferably treated by administering the medicament over a number of days, for example over a period of from 5 to 20 days, followed by a treatment break and, where appropriate, by one or more administration repeats.

The following examples and figures are intended to illustrate the invention in more detail. In the figures.

EXAMPLES

1. Nα-2,4,6-Triisopropylphenylsulfonyl-(L)-3-amidinophenylalanine 4-Ethoxycarbonylpiperazide Hydrochloride 1.1 Nα-2,4,6-Triisopropylphenylsulfonyl-(L)-3-cyanophenylalanine Methyl Ester 5 g of (L)-3-cyanophenylalanine methyl ester were suspended in 100 ml of dioxane, 4.45 ml of N-methylmorpholine (NMM) were added and the mixture was stirred for 30 min. After adding 5.97 g of 2,4,6-triisopropylbenzenesulfonyl chloride in solid form and subsequent stirring for 3 days, precipitated NMM-HCl was filtered off, the solvent was distilled off and the crude product obtained was purified on silica gel (SG) 60 (chloroform). Yield: 8.34 g of syrup (90%).

1.2 Nα-2,4,6-Triisopropylphenylsulfonyl-(L)-3-cyanophenylalanine 8.34 g of compound 1.1 were heated under reflux in a mixture of 50 ml each of acetic acid and 1 N hydrochloric acid for 8 h and, after cooling, extracted twice with ethyl acetate; the combined ethyl acetate solutions were dried over MgSO$_4$ and the solvent was distilled off. After purification on SG 60 (chloroform), 5.8 g of a solid product were obtained (72%).

1.3 Nα-2,4,6-Triisopropylphenylsulfonyl-(L)-3-cyanophenylalanine 4-Ethoxycarbonylpiperazide 5.7 g of compound 1.2 were dissolved in 100 ml of tetrahydrofuran (THF) and cooled to 0° C.; 2.22 g of α-hydroxybenzotriazole (HOBt) and 2.82 g of dicyclohexylcarbodiimide (DCC) were added and the mixture was stirred for 30 min. After adding 3.94 g of 1-ethoxycarbonylpiperazine in 30 ml of THF and subsequent stirring overnight, precipitated dicyclohexylurea (DCU) was filtered off, the solvent was distilled off and the crude product obtained was purified on SG 60 (chloroform). Yield: 7.1 g of an amorphous powder (96%).

1.4. Nα-2,4, 6-Triisopropylphenylsulfonyl-(L)-3-amidinophenylalanine 4-Ethoxycarbonylpiperazide Hydrochloride 7.1 g of compound 1.3 were dissolved in 30 ml of pyridine, 30 drops of triethanolamine (TEA) were added, a vigorous stream of hydrogen sulfide was introduced for 10 min, and the mixture was left at room temperature for 2 days. The solvent was then distilled off, the residue was dissolved in ethyl acetate, the organic phase was washed with 1 N hydrochloric acid and saturated sodium chloride solution and dried over MgSO$_4$, and the solvent was distilled off. 7.2 g of thioamide obtained in this way were dissolved in 250 ml of acetone, 17 g of methyl iodide were added to the solution, and the mixture was left at room temperature under protection from light for 2 days. The solvent was then distilled off, the thioimido ester hydroiodide (8.5 g) was dissolved in 50 ml of methanol, 1.9 g of ammonium acetate were added and the mixture was heated to 60° C. for 4 h. After distilling off the solvent, the crude product obtained was purified on Sephadex LH20 (methanol). The amidine hydroiodide obtained in this way was converted into the hydrochloride via an ion exchange column (Amberlite IRA-420). Yield: 5.3 g of an amorphous powder (69%).

2. Nα-2,4,6-Triisopropylphenylsulfonyl-(D,L)-3-amidinophenylalanylnipecotic Acid Benzylamide Hydrochloride 2.1 Ethyl Nα-2,4,6-Triisopropylphenylsulfonyl-(D,L)-3-cyanophenylalanylnipecotate 4.56 g of Nα-2,4,6-triisopropylphenylsulfonyl-(D,L)-3-cyanophenylalanine (prepared from (D,L)-3-cyanophenylalanine methyl ester hydrochloride and the appropriate sulfonyl chloride analogously to 1.1 and 1.2), 1.5 g of HOBt and 2.42 g of DCC were dissolved in 50 ml of DMF; the mixture was stirred for 1 h, and then 2.36 g of ethyl nipecotate were added. After stirring overnight, precipitated DCU was filtered off, the solvent was distilled off and the residue was dissolved in a small amount of methanol and left to crystallize. The precipitate formed was filtered off with suction, washed with methanol and dried. Yield: 4.46 g (75%).

2.2 Nα-2,4,6-Triisopropylphenylsulfonyl-(D,L)-3-cyanophenylalanylnipecotic Acid 4.4 g of the above-described ethyl ester were heated under reflux in a mixture of 35 ml of acetic acid and 25 ml of 1 N HCl for 2 h. After adding 10 ml of water, the mixture was left to cool, and a wax-like product precipitated. After decanting the solvent, 200 ml of water were added, the mixture was stirred over a relatively long period, and the solid substance obtained was filtered off with suction, washed with water and dried. Yield: 3.84 g (92%).

2.3 Nα-2,4,6-Triisopropylphenylsulfonyl-(D,L)-3-cyanophenylalanylnipecotic Acid Benzylamide 2.28 g of the above-described compound, 0.6 g of HOBt and 0.97 g of DCC were dissolved in 20 ml of DMF and the mixture was stirred for 1 h; 0.6 g of benzylamine was then added, and stirring continued overnight. After filtering off the precipitated DCU, the solvent was distilled off, the residue was dissolved in methanol and the solution was poured into 5% strength sodium hydrogen carbonate solution/ice. After 1 h, the precipitate formed was filtered off with suction, washed with water and dried in vacuo. Yield: 2.48 g (94%).

2.4 Nα-2,4,6-Triisopropylphenylsulfonyl-(D,L)-3-amidinophenylalanylnipecotic Acid Benzylamide Hydrochloride 2.4 g of compound 2.3 were dissolved in 30 ml of pyridine, 30 drops of triethanolamine (TEA) were added, a vigorous stream of hydrogen sulfide was introduced for 10 min, and the mixture was left at room temperature for 2 days. The solvent was then distilled off, the residue was dissolved in ethyl acetate, and extracted with 1 N hydrochloric acid.

After washing the organic phase with saturated sodium chloride solution and drying over sodium sulfate, the solvent was distilled off. 2.38 g of the thioamide obtained in this way were dissolved in 100 ml of acetone, 6.5 g of methyl iodide were added to the solution, and the mixture was left at room temperature under protection from light for 20 h. The solvent was then distilled off, the thioimido ester hydroiodide was dissolved in 50 ml of methanol, 0.5 g of ammonium acetate was added and the mixture was heated to 60° C. in a water bath for 4 h. After distilling off the solvent, the crude product obtained was purified on SG 60. Elution was carried out first with chloroform, then with chloroform/methanol 9:1. The amidine hydroiodide obtained in this way was converted into the hydrochloride on an ion exchange column (Amberlite IRA-420). Yield: 1.45 g of an amorphous powder (56%).

The compounds were characterized using mass spectrometry, and purity was checked by means of TLC and HPLC.

3. In vitro Inhibition of Urokinase by Selected Compounds of the Formula I

| Configuration | $R^1$ | $R^2$ | n | Ki, $\mu$mol/l |
|---|---|---|---|---|
| L | —N N—COOC$_2$H$_5$ | TIPP | 0 | 0.41 |
| D,L | —N N—COOC$_2$H$_5$ | TIPP | 0 | 0.96 |

Abbreviations: TIPP—2,4,6-Triisopropylphenyl

Determination of Inhibition Activity

To determine the inhibitory activity, 200 $\mu$l of Tris buffer (0.05 mol/l, containing the inhibitor, 0.154 mol/l NaCl, 5% ethanol pH 8.0), 25 $\mu$l of substrate (Pefachrome UK or Bz-βAla-Gly-Arg-pNA in H$_2$O; Pentapharm Ltd., Basle, Switzerland) and 50 $\mu$l of scurokinase (Ribosepharm GmbH, Haan, Germany) were incubated at 25° C. After 3 min the reaction was stopped by adding 25 $\mu$l of acetic acid (50%), and the absorption at 405 nm was determined by means of a Microplate Reader (MR 5000, Dynatech, Denkendorf, Germany). $K_i$ values were determined according to Dixon by linear regression using a computer program. The $K_i$ values are the mean values of at least three determinations with a standard deviation of less than 25%.

4. In vitro Inhibition of Various Serine Proteases of the Trypsin Type by (Nα-2,4,6-Triisopropylphenylsulfonyl-(L)-3-amidinophenylalanine 4-Ethoxycarbonylpiperazide (uPA Inhibitor) Compared With Nα-2-Naphthylsulfonyl-3-amidinophenylalanine N'-Methylpiperazide (Naphthylsulfonyl Derivative)

| | Ki [$\mu$mol/l] | |
|---|---|---|
| Enzyme | uPA-Inh. | Naphthylsulfonyl derivative |
| Urokinase | 0.41 | 150 |
| Plasmin | 0.39 | 55 |
| Sc-tPA | 4.9 | 430 |
| Thrombin | 0.49 | 0.036 |
| Factor Xa | 1.7 | 30 |
| Factor XIIa | 13 | >1000 |
| Plasma kallikrein | 7.2 | 85 |
| Glandular kallikrein | >1000 | >1000 |
| Trypsin | 0.037 | 1.3 |
| Tryptase | 6.3 | 33 |

The inhibition activities of the enzymes used were determined according to the principle described in Example 3.

The values given above indicate that the uPA inhibitor according to the invention has a $K_i$ or urokinase which according to the invention has a $K_i$ for urokinase which is more than ten times smaller than the $K_i$ for single chain tPA (Sc-tPA). Thus, the substances of the invention are suitable as selective urokinase inhibitors. For comparison, the inhibitory activity of the naphthylsulfonyl derivative is given which has a significantly lower in vitro anti-uPA activity.

5. Cytotoxicity Determination

Figure 1:
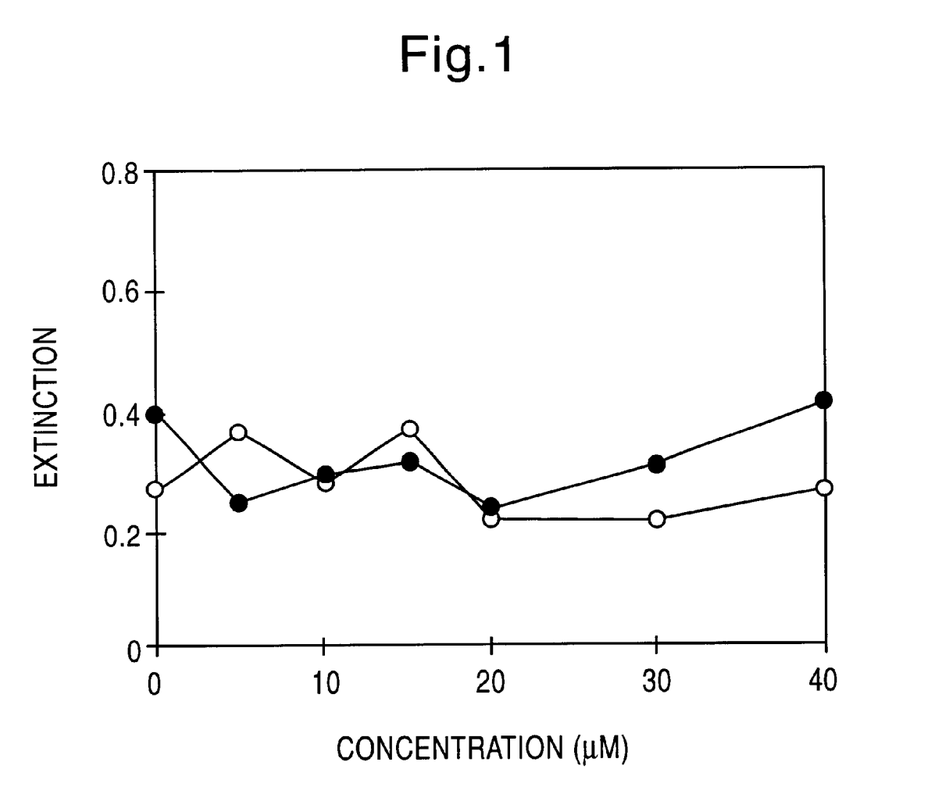
FIG. 1 depicts the result from determining the cytotoxicity of a substance of the invention.

To determine cell proliferation/cytotoxicity a commercially available test was used (Promega) which is based on the cellular conversion of a tetrazolium salt. The colored product resulting from this reaction can be quantified by means of an ELISA spectrometer (ICN flow). The synthetic inhibitor (open circles) had no effect on the growth of the human ovarian carcinoma cells OV-MZ-6 (FIG. 1) when compared with the solvent alone (closed circles). Thus, the inventive uPA inhibitor is not cytotoxic in pharmacologically effective concentrations up to 40 $\mu$M.

6. Inhibition of the Degradation by Human Breast Carcinoma Cells of a Fibrin Matrix To study the potential of tumor cells for breaking down an extracellular matrix, a fibrin matrix degradation assay was developed and used. A greater proteolytic activity of the tumor cells leads to a higher concentration of fibrin degradation products in the matrix supernatant. The matrix degradation capacity corresponds to the concentration of fibrin degradation products which are determined by means of ELISA (D dimer).

Figure 2:
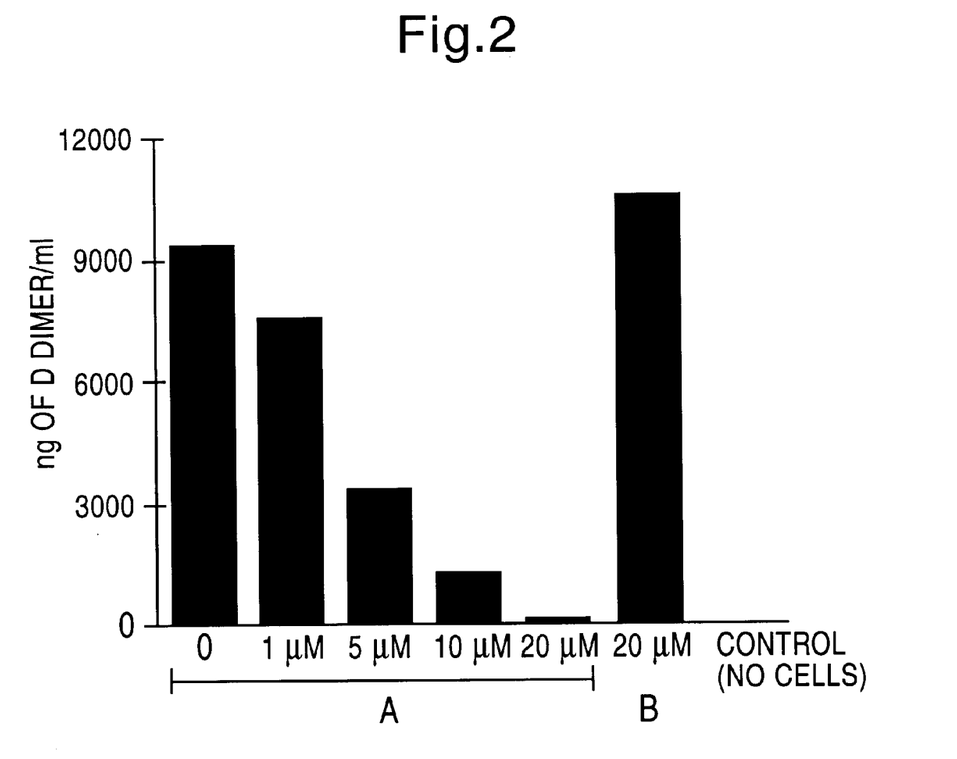
FIG. 2 depicts the experimental result from inhibiting the degradation by human breast carcinoma cells of a fibrin matrix.

The fibrin gels were prepared in 24-well culture dishes from 200 ml of fibrinogen (50 mg/ml) in PBS (pH 7.4), by 50 $\mu$l of thrombin (10 U/ml) and 50 $\mu$l of CaCl$_2$ (150 mM) per well after incubation at 37° C. for 30 minutes. 2×10$^5$ breast carcinoma cells were seeded on said fibrin matrix in 1 ml of DDEM culture medium plus 10% fetal calf serum and 2 $\mu$g of Glu-plasminogen, and incubated for 4 h. The supernatant was then centrifuged, in order to remove the cells, and the fibrin degradation products were quantified by means of ELISA. Adding the inhibitor (A) at different concentrations caused significant inhibition of matrix degradation by breast carcinoma cells compared with the naphthyl derivative (B) which shows no inhibition of fibrin degradation by breast carcinoma cells (FIG. 2).

7. In vitro Assay of the UPA Inhibitor for Tumor Spreading, Tumor Growth and Metastasizing in Rats A) Breast Cancer Model 10–25 mm$^3$ of BN-472 breast cancer tumor fragments from rats were transplanted into female brown Norwegian rats from 6 to 7 weeks old, subcutaneously and orthotopically under the subcutaneous fat of the mammary gland (Day 0). The treatment of the animals was started intraperitoneally 24 hours after tumor inoculation. Each group consisted of eight animals. The control group received only the injection solution (100 $\mu$l of a 10% ethanol/saline (0.9% NaCl) solution). A dose of 1 mg/kg body weight was intraperitoneally administered on a daily basis to the comparative group of the naphthyl derivative (B) and to the therapy group of the inventive uPA inhibitor (A). The treatment was carried out over a period of 4 weeks.

The dimensions of the subcutaneous tumors and the weight of the animals were determined weekly. At the end of the treatment the animals were sacrificed and tumor weights, organ weights and the number of metastases in relevant tissues were determined.

Figure 3:
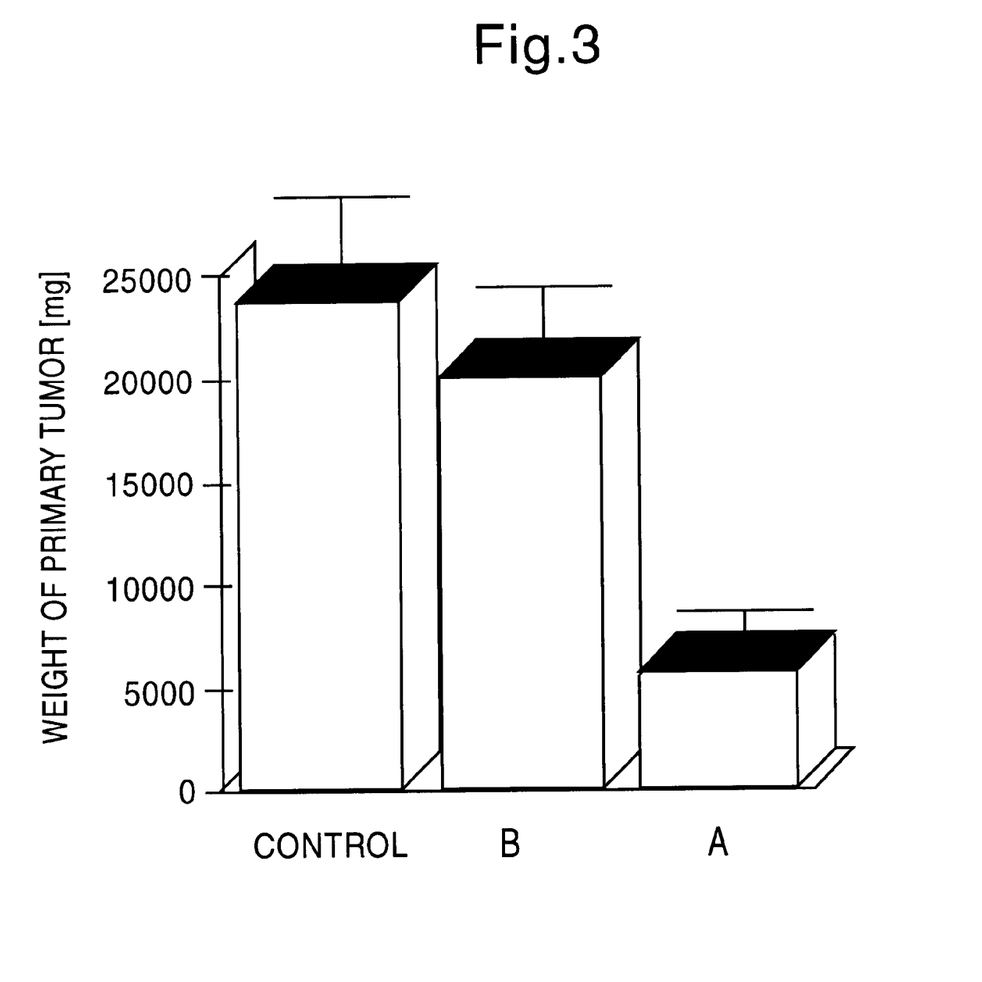
FIGS. 3 and 4 depict the effect of a substance of the invention on the spreading, growth and metastasizing of breast carcinoma cells in rats.
Figure 4:
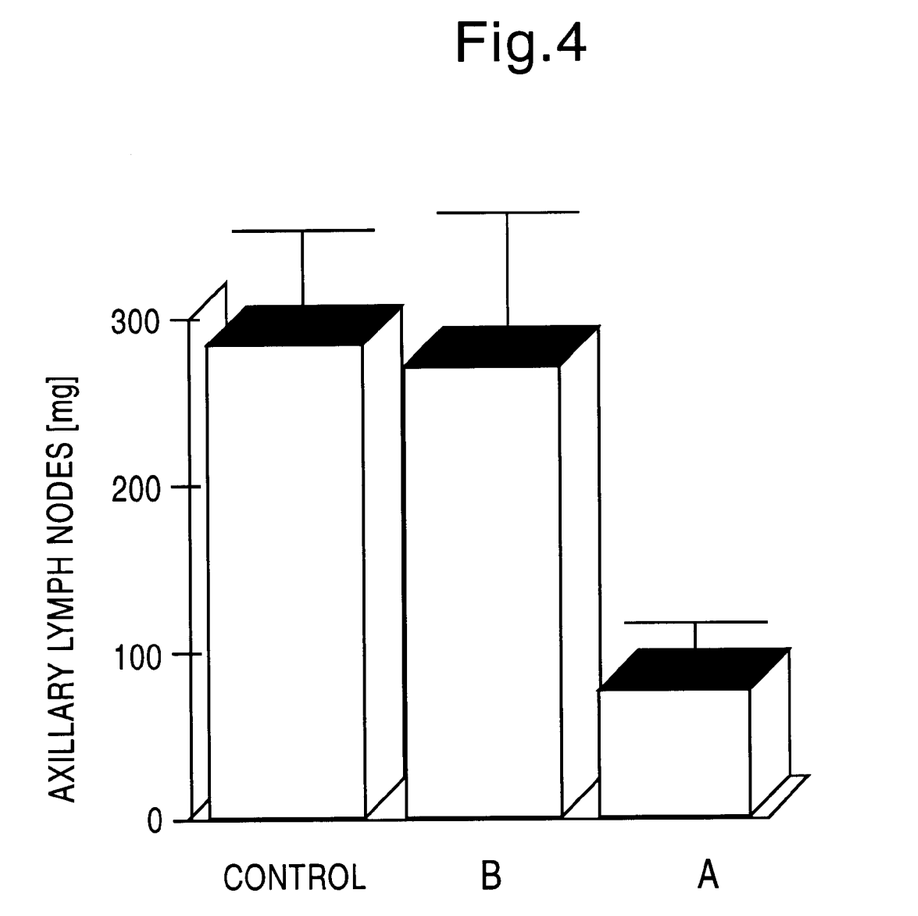

Treatment with uPA inhibitor (A) resulted in a significant reduction in the weight of the primary tumor and also of the axillary lymph nodes (p=0.003 and p=0.005) compared with the naphthyl derivative (B) and control groups without inhibitor (FIGS. 3 and 4). The weights of lung, liver, kidney and spleen were unchanged in the animals treated with the uPA inhibitor compared to the control animals.

B) Pancreatic Carcinoma Model

Fragments of the transplantable and metastasizing pancreatic adenocarcinoma CA20948 from rats were explanted from donor animals. After cell isolation, equal amounts of suspended tumor cells together with 2 mg of Matrigel were subcutaneously implanted into each of the acceptor animals, male 10 week-old Lewis rats (n=9). The treatment procedure and also the composition of the therapy groups were the same as under A).

Figure 5:
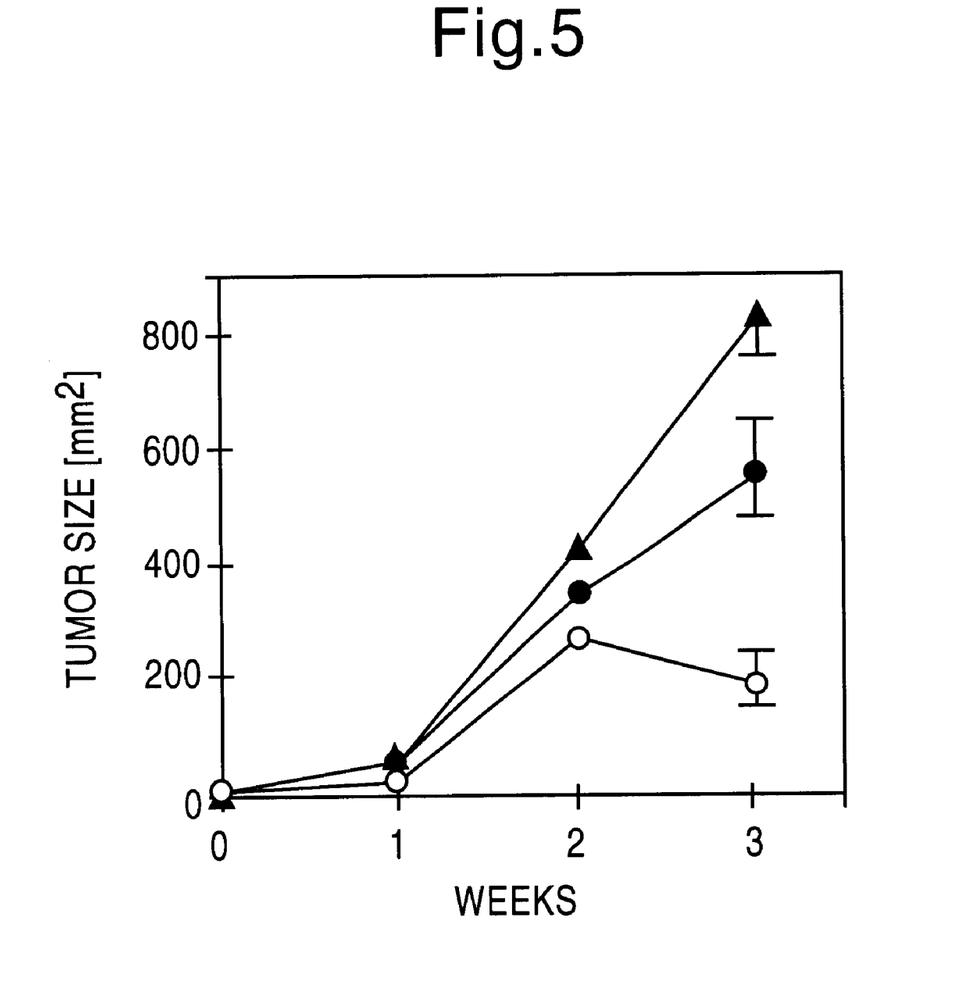
FIG. 5 depicts the effect of a substance of the invention on the growth of a pancreatic tumor in rats.

FIG. 5 shows for the inventive uPA inhibitor (open circles) a significant reduction in tumor weight and a decrease in the growth of developing rat pancreatic carcinomas compared to the naphthyl derivative (closed circles) and the control group (triangles).

C) Repeat of the Experiments With Different Mode of Administration

The experiments described in sections A and B were repeated with the inhibitor administered in a different way. For this, the inhibitor was administered subcutaneously in the breast carcinoma model (n=9) and intraperitoneally in the pancreatic adenocarcinoma model (n=8) without changing the daily dose. The results of these repeat experiments corresponded to the results already discussed, both in tendency and extent.

D) Summary of the Results

Treatment with the inhibitor achieved in all experiments a considerable reduction in tumor size and tumor weight and in the number and mass of metastases in comparison with the control groups. In the inhibitor-treated group of the breast tumor model, the average tumor weights at the end of the treatment were reduced to 23% (i.p.) or 37% (s.c.) compared to the vehicle-treated control. The number of lung foci in inhibitor-treated groups was reduced to 9% (i.p.) or 32% (s.c.) and the mean weights of the axillary lymph nodes to 27% (i.p.) or 48% (s.c.).

In the inhibitor-treated groups of the pancreatic tumor model, the mass of the tumor-containing pancreas was reduced by 76% (i.p.) or 34% (s.c.), and the masses of the subcutaneous tumors by 54% (i.p.) or 60% (s.c.), compared to the respective vehicle-treated groups. The number of detected liver foci in inhibitor-treated groups was 29% (i.p.), or 2% (s.c.), compared to the vehicle-treated control groups.

The development of the body weight increase and comparison of the organ weights between inhibitor-treated and vehicle-treated groups showed no indications of any considerable toxicity of the inhibitor under the described conditions.

8. Treatment of Human Breast Cancer Cells in Nude Mice

In order to test the in vivo efficacy of the inhibitor for inhibiting tumor growth of human breast carcinoma cells (MDA-BA-231), $6 \times 10^6$ cells were injected subcutaneously into the right flank of Balb/c nude mice (4–6 weeks old). The tumor cells were preincubated with the synthetic uPA inhibitor prior to inoculation. After 24 h, the mice were treated twice a week intraperitoneally with a dose of 1.2 mg/kg body weight as described under A). The tumor size was determined weekly by measuring the two largest diameters.

Figure 6:
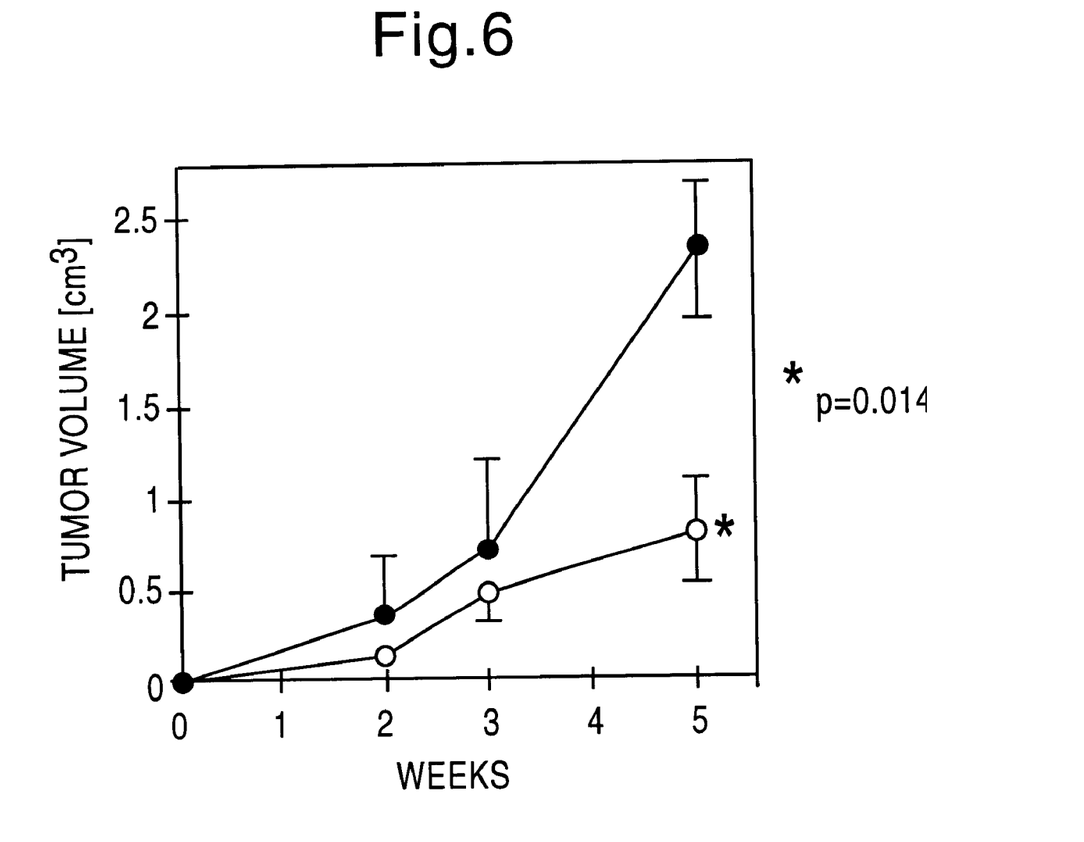
FIG. 6 depicts the effect of a substance of the invention on the growth of human breast carcinoma cells in mice.

FIG. 6 shows that the tumor volume increases significantly more slowly on administration of the uPA inhibitor (open circles) than in the control group (closed circles) in which ethanol in saline was administered.

9. Biodistribution of the Inhibitor in Rats

The biodistribution of the inhibitor was determined by two independent experiments in tissue extracts of rats which had been treated once a day with 1 mg/kg i.p. of inhibitor i.p. over a period of 5 or 10 days. For the lysis, in each case 100 mg of tissue were mechanically comminuted and mixed with 200 µl of 1% Triton X-100 in physiological NaCl solution. After adding 400 µl of ethanol, the mixture was sonicated for 1 min. The tissue extract was centrifuged at 12,000×g for 15 min. For prepurification, the supernatant was applied to a $C_{18}$ Silica Reversed Phase column (Sep-Pak® cartridge C18, 1 ml Water, Eschborn, Germany), equilibrated with 1 ml of methanol and 1 ml of water, washed successively with 2×1 ml $H_2O$, 1 ml 10% methanol, 1 ml $H_2O$, 1 ml 5% acetonitrile, 0.04% perchloric acid and 1 ml $H_2O$ and eluted with 500 µl of 75% acetonitrile, 0.04% perchloric acid. HPLC analysis was carried out on a reversed phase C18 silica column with a 5–55% strength acetonitrile gradient containing 0.04% perchloric acid.

The concentrations of the inhibitor and, for comparison, of a corresponding naphthylsulfonyl derivative in each of the tissue types studied (µg/g) and also in blood plasma and bile (µg/ml) are depicted in the following table.

TABLE

Distribution profile of a substance of the invention in various tissues and in blood plasma and bile in comparison with a naphthylsulfonyl derivative (Nα-2-naphthylsulfonyl-3-amidinophenylalanine 4-ethoxy-carbonylpiperazide

| | Content (µg/g) | | |
|---|---|---|---|
| Tissue | uPA inhibitor 1 mg/kg i.p. 5 days | uPA inhibitor 1 mg/kg i.p. 10 days | Naphthyl-sulfonyl derivative 1 mg/kg i.p. 5 days |
| Spleen | 2.02 | 2.48 | 0.089 |
| Liver | 2.85 | 2.08 | 0.12 |
| Kidney | 2.67 | 2.48 | 0.085 |
| Muscle | 0.74 | <0.5 | 0.008 |
| Fat/kidney | 0.82 | 1.0 | <0.005 |
| Heart | <0.5 | 1.09 | 0.59 |
| Lung | 3.70 | 1.81 | 0.020 |
| Brain | <0.5 | <0.5 | |
| Lymph nodes/trachea | 7.45 | 16.38 | 0.12 |
| lymph nodes/axillary | 1.97 | 2.74 | <0.005 |
| lymph nodes/knee | 7.83 | 3.8 | <0.005 |

Content (µg/ml)

TABLE-continued

Distribution profile of a substance of the invention in various tissues and in blood plasma and bile in comparison with a naphthylsulfonyl derivative (Nα-2-naphthylsulfonyl-3-amidinophenylalanine 4-ethoxy-carbonylpiperazide

| Tissue | Content (μg/g) | | |
| --- | --- | --- | --- |
| | uPA inhibitor 1 mg/kg i.p. 5 days | uPA inhibitor 1 mg/kg i.p. 10 days | Naphthyl-sulfonyl derivative 1 mg/kg i.p. 5 days |
| Plasma | 0.008 | 0.035 | 0.004 |
| Bile | 1.96 | 1.75 | 0.097 |

In most of the tissue types studied, the inhibitor was present at from 1 to 3 μg/g after 5 to 10 days. 24 h after the last i.p. administration in each case, the plasma concentrations of the inhibitor were in each case one to two orders of magnitude below the mean tissue concentrations. From this, high tissue affinity and low plasma protein binding can be concluded. The concentrations of the naphthylsulfonyl derivative, administered for comparison over 5 days, were 20–30 times lower in the various tissues.

The inhibitor shows a noticeable accumulation in lymph nodes. In the independent experiments, concentrations of 5.3 and 7.5 μg/g, respectively, were measured in tracheal lymph nodes after 5 days of administration, and concentrations of 21.6 and 16.4 μg/g, respectively, after 10 days of administration. Since tumor cells often disseminate via lymph tracts, the specific accumulation of the inhibitor in lymphatic vessels is important and advantageous for its use as an anti-metastatic therapeutic agent.

What is claimed is:

1. A method of treating a urokinase-associated or urokinase receptor-associated disorder in a patient in need of such treatment, comprising administering to the patient a therapeutic amount of a compound of formula I which is present as a racemate or as D- or L-enantiomers and in which $R^1$ is selected from the group consisting of piperidine and piperazine, wherein said piperidine and said piperazine, independently, are each optionally substituted with $C_1$–$C_8$ alkyl, $C_1$–$C_3$ alkoxy, hydroxy, carboxyl, sulfonyl, nitro, cyano, oxo, halo or a combination thereof, $R^2$ is 2, 4, 6 trisubstituted phenyl, $R^3$ is H or branched or unbranched $C_1$–$C_4$-alkyl, and n is 0 or 1, or a salt of said compound.

2. A method as claimed in claim 1, wherein $R^1$ is selected from the group consisting of piperidine and piperazine, wherein said piperidine and said piperazine, independently, are each optionally substituted with $C_1$–$C_8$ alkoxycarbonyl.

3. The method of claim 1, wherein said compound of formula I is Nα-(2,4,6-triisopropylphenylsulfonyl)-3-amidino-(D,L)-phenylalanine 4-ethoxycarbonylpiperazide or a pharmaceutically suitable salt thereof.

4. The method of claim 1, characterized in that the compounds are present in the form of physiologically acceptable acid salts.

5. The method of claim 4, wherein said physiologically acceptable acid salt is a hydrochloride.

6. The method as claimed in claim 1, wherein the compounds of the formula I are used coupled with further pharmacologically active substances.

7. The method as claimed in claim 1, wherein the compounds are used coupled with radiolabels or with cytotoxic substances.

8. The method of claim 1, wherein the method is a method of controlling tumors.

9. The method of claim 1, wherein the method controls breast carcinomas, pancreatic carcinomas or the formation of metastases.

10. The method of claim 1, wherein the method is for controlling pemphigus vulgaris.

11. The method of claim 1, wherein the compound is administered orally, topically, rectally or parenterally.

12. The method of claim 1, wherein the compound is administered in the form of a tablet, a coated tablet, a capsule, a pellet, a suppository, a solution or transdermal system.

13. A method for inhibiting urokinase in living creatures by administering an effective quantity of at least one urokinase inhibitor as claimed in claim 1.

14. The method of claim 13, wherein said living creature is a human.

* * * * *

UNITED STATES PATENT AND TRADEMARK OFFICE
CERTIFICATE OF CORRECTION

PATENT NO.     : 6,624,169 B1
DATED          : September 23, 2003
INVENTOR(S)    : Olaf Wilhelm et al.

It is certified that error appears in the above-identified patent and that said Letters Patent is hereby corrected as shown below:

<u>Title page,</u>
Item [73], please correct the Assignee's name to -- Wilex AG. --

Signed and Sealed this

Twenty-seventh Day of January, 2004

JON W. DUDAS
*Acting Director of the United States Patent and Trademark Office*

UNITED STATES PATENT AND TRADEMARK OFFICE
CERTIFICATE OF CORRECTION

| | |
|---|---|
| PATENT NO. | : 6,624,169 B1 |
| APPLICATION NO. | : 09/743800 |
| DATED | : September 23, 2003 |
| INVENTOR(S) | : Olaf Wilhelm et al. |

It is certified that error appears in the above-identified patent and that said Letters Patent is hereby corrected as shown below:

Insert claim 15 as shown below:

15. A method of treating a urokinase-associated or urokinase receptor-associated disorder in a patient in need of such treatment, comprising administering to the patient a therapeutic amount of Nα (2,4,6-triisopropylphenylsulfonyl)-3-amidino-(L)-phenylalanine-4-ethoxycarbonylpiperazide or a pharmaceutically suitable salt thereof.

Signed and Sealed this

Twelfth Day of September, 2006

JON W. DUDAS
*Director of the United States Patent and Trademark Office*